US010744332B2

United States Patent
Carroll et al.

(10) Patent No.: US 10,744,332 B2
(45) Date of Patent: *Aug. 18, 2020

(54) BIOSTIMULATOR CIRCUIT WITH FLYING CELL

(71) Applicant: Pacesetter, Inc., Santa Clara, CA (US)

(72) Inventors: Kenneth J. Carroll, Los Altos, CA (US); Alan Ostroff, Pleasanton, CA (US); Peter M. Jacobson, Livermore, CA (US)

(73) Assignee: Pacesetter, Inc., Sylmar, CA (US)

( * ) Notice: Subject to any disclaimer, the term of this patent is extended or adjusted under 35 U.S.C. 154(b) by 319 days.

This patent is subject to a terminal disclaimer.

(21) Appl. No.: 15/712,497

(22) Filed: Sep. 22, 2017

(65) Prior Publication Data

US 2018/0008833 A1     Jan. 11, 2018

Related U.S. Application Data

(62) Division of application No. 13/956,946, filed on Aug. 1, 2013, now Pat. No. 9,802,054.

(Continued)

(51) Int. Cl.
*A61N 1/375*     (2006.01)
*A61N 1/372*     (2006.01)
*A61N 1/362*     (2006.01)

(52) U.S. Cl.
CPC .......... *A61N 1/3756* (2013.01); *A61N 1/362* (2013.01); *A61N 1/3758* (2013.01); *A61N 1/37205* (2013.01); *A61N 1/375* (2013.01)

(58) Field of Classification Search
CPC .... A61N 1/362; A61N 1/3756; A61N 1/3758; A61N 1/37205; A61N 1/375
See application file for complete search history.

(56) References Cited

U.S. PATENT DOCUMENTS 3,199,508 A    8/1965   Roth
3,212,496 A    10/1965   Preston
(Continued)

FOREIGN PATENT DOCUMENTS

EP     0 801 958 A1    10/1997
EP     1741465 A1    1/2007
(Continued)

OTHER PUBLICATIONS

International Search Report dated Nov. 22, 2013; Related Serial No. PCT/U52013/053217. WO.

(Continued)

*Primary Examiner* — Christopher Koharski
*Assistant Examiner* — Pamela M. Bays
(74) *Attorney, Agent, or Firm* — Vierra Magen Marcus LLP

(57) ABSTRACT

A leadless cardiac pacemaker is provided which can include any number of features. In one embodiment, the pacemaker can include a tip electrode, pacing electronics disposed on a p-type substrate in an electronics housing, the pacing electronics being electrically connected to the tip electrode, an energy source disposed in a cell housing, the energy source comprising a negative terminal electrically connected to the cell housing and a positive terminal electrically connected to the pacing electronics, wherein the pacing electronics are configured to drive the tip electrode negative with respect to the cell housing during a stimulation pulse. The pacemaker advantageously allows p-type pacing electronics to drive a tip electrode negative with respect to the can electrode when the can electrode is directly connected to a negative terminal of the cell. Methods of use are also provided.

14 Claims, 4 Drawing Sheets

Related U.S. Application Data

(60) Provisional application No. 61/678,505, filed on Aug. 1, 2012.

(56) References Cited

U.S. PATENT DOCUMENTS

| | | | |
|---|---|---|---|
| 3,218,638 A | 11/1965 | Honig |
| 3,241,656 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,243,977 A | 9/1993 | Trabucco et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |

(56) References Cited

U.S. PATENT DOCUMENTS

| | | |
|---|---|---|
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,642,014 A | 6/1997 | Hillenius |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |

(56) References Cited

U.S. PATENT DOCUMENTS

| | | |
|---|---|---|
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marciavecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dimberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,177,698 B2 | 2/2007 | Klosterman et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,684,864 B2 | 3/2010 | Olson et al. |
| 7,848,823 B2 | 12/2010 | Drasler et al. |
| 7,937,148 B2 | 5/2011 | Jacobson |

(56) References Cited

U.S. PATENT DOCUMENTS

| | | | |
|---|---|---|---|
| 7,945,333 B2 | 5/2011 | Jacobson |
| 8,010,209 B2 | 8/2011 | Jacobson |
| 8,295,939 B2 | 10/2012 | Jacobson |
| 8,352,025 B2 | 1/2013 | Jacobson |
| 8,457,742 B2 | 6/2013 | Jacobson |
| 8,527,068 B2 | 9/2013 | Ostroff |
| 8,543,205 B2 | 9/2013 | Ostroff |
| 8,788,035 B2 | 7/2014 | Jacobson |
| 8,798,745 B2 | 8/2014 | Jacobson |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075677 A1* | 4/2005 | Ganion ............. A61N 1/3627 607/9 |
| 2005/0075682 A1 | 4/2005 | Schulman et al. |
| 2005/0082942 A1 | 4/2005 | Shirley |
| 2005/0096702 A1 | 5/2005 | Denker et al. |
| 2005/0131478 A1 | 6/2005 | Kim et al. |
| 2005/0136385 A1 | 6/2005 | Mann et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088396 A1 | 4/2007 | Jacobson |
| 2007/0088397 A1 | 4/2007 | Jacobson |
| 2007/0088405 A1 | 4/2007 | Jacobson |
| 2007/0123923 A1 | 5/2007 | Lindstrom et al. |
| 2007/0135883 A1* | 6/2007 | Drasler ............. A61B 5/6882 607/126 |
| 2007/0142709 A1 | 6/2007 | Martone et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock et al. |
| 2010/0211149 A1 | 8/2010 | Morgan et al. |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0282423 A1 | 11/2011 | Jacobson |
| 2012/0095539 A1 | 4/2012 | Khairkhahan et al. |
| 2012/0109236 A1 | 5/2012 | Jacobson et al. |
| 2012/0116483 A1* | 5/2012 | Yonezawa ............. A61N 1/36 607/74 |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2012/0245665 A1 | 9/2012 | Friedman et al. |
| 2013/0041422 A1 | 2/2013 | Jacobson |
| 2013/0103109 A1 | 4/2013 | Jacobson |
| 2013/0123875 A1 | 5/2013 | Varady et al. |
| 2013/0231710 A1 | 9/2013 | Jacobson |
| 2013/0261497 A1 | 10/2013 | Pertijs et al. |
| 2013/0274847 A1 | 10/2013 | Ostroff |
| 2013/0324825 A1 | 12/2013 | Ostroff et al. |
| 2014/0039570 A1 | 2/2014 | Carroll et al. |

FOREIGN PATENT DOCUMENTS

| | | |
|---|---|---|
| JP | H04-506167 | 10/1992 |
| JP | 05-245215 | 9/1993 |
| JP | 06/507096 | 3/2006 |
| JP | 06/516449 | 7/2006 |
| JP | 2006-526483 | 11/2006 |
| WO | 93/12714 A1 | 7/1993 |
| WO | 02/34333 A2 | 5/2002 |
| WO | 04/012811 | 2/2004 |
| WO | 2006/065394 A1 | 6/2006 |
| WO | 2007/047681 A2 | 4/2007 |
| WO | 2007/059386 A2 | 5/2007 |
| WO | WO 2008/058265 A2 | 5/2008 |
| WO | WO2010/088116 A1 | 8/2010 |
| WO | 2014/022661 A1 | 2/2014 |

OTHER PUBLICATIONS

International Searching Authority, "Notification of Transmittal of the International Search Report and the Written Opinion of the International Searching Authority, or the Declaration," International Application No. PCT/US12/63552, dated Feb. 22, 2018, 11 pages.

Notice of Allowance dated Jul. 19, 2017; Related U.S. Appl. No. 13/956,946.

Non-Final Office Action dated Apr. 7, 2017; Related U.S. Appl. No. 13/956,946.

Amendment filed Apr. 7, 2017; Related U.S. Appl. No. 13/956,946.

Advisory Action dated Nov. 3, 2016; Related U.S. Appl. No. 13/956,946.

Amendment filed Sep. 1, 2016; Related U.S. Appl. No. 13/956,946.

Final Office Action dated Aug. 10, 2016; Related U.S. Appl. No. 13/956,946.

Amendment filed Apr. 20, 2016; Related U.S. Appl. No. 13/956,946.

Non-Final Office Action dated Jan. 21, 2016; Related U.S. Appl. No. 13/956,946.

Advisory Action dated Sep. 25, 2016; Related U.S. Appl. No. 13/956,946.

(56) References Cited

OTHER PUBLICATIONS

Amendment filed Sep. 25, 2015; Related U.S. Appl. No. 13/956,946.
Amendment filed Jul. 14, 2015, Related U.S. App. No. 13/956,946.
Final Office Action dated May 27, 2015, Related U.S. Appl. No. 13/956,946.
Amendment filed Jan. 23, 2015; Related U.S. Appl. No. 13/956,946.
Amendment filed Dec. 23, 2014; U.S. Appl. No. 13/956,946.
Non-Final Office Action dated Aug. 29, 2014; U.S. Appl. No. 13/956,946.
U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of the app. is U.S. Pat. No. 7,630,767).
Beeby et al.; Micromachined silicon generator for harvesting power from vibrations; (Proceedings) PowerMEMS 2004; Kyoto, Japan; pp. 104-107; Nov. 28-30, 2004.
Bordacher et al.; Impact and prevention of far-field sensing in fallback mode switches; PACE; vol. 26 (pt. II); pp. 206-209; Jan. 2003.
Brandt et al.; Far-field QRS complex sensing: prevalence and timing with bipolar atrial leads; PACE; vol. 23; pp. 315-320; Mar. 2000.
Brown, Eric S.; The atomic battery; Technology Review: Published by MIT; 4 pgs.; Jun. 16, 2005.
Irnich et al.; Do we need pacemakers resistant to magnetic resonance imaging; Europace; vol. 7; pp. 353-365; Feb. 2005.
Irnich; Electronic security systems and active implantable medical devices; Journal of PACE; vol. 25; No. 8; pp. 1235-1258; Aug. 2002.
Luechinger et al.; Force and torque effects of a 1.5-tesla MRI scanner of cardiac pacemakers and ICDs; Journal of PACE; vol. 24; No. 2; pp. 199-205; Feb. 2001.
Luechinger et al.; In vivo heating of pacemaker leads daring magnetic resonance imaging; European Heart Journal; vol. 26: pp. 376-383; Feb. 2005.
Lüchinger ; Satiety aspects of cardiac pacemakers in magnetic resonance imaging; Dissertation submitted to the Swiss Federal Institute of Technology Zurich; 137 pages; (year at publication is sufficiently earlier than the effective U.S. filing date and any foreign priority date) 2002.
Nyeniauis et al.; MRI and Implanted Medical Device: Basic Interactions with an emphasis on heating: vol. 5; No. 3; pp. 467-480; Sep. 2005.
Shellock et al.; Cardiac pacemaker: In vitro assessment at 1.5 T; Am Heart J; vol. 151; No. 2; pp. 436-443; Feb. 2006.
Pertijs et al.; U.S. Appl. No. 13/901,414 entitled "Temperature Sensor for a Leadless Cardiac pacemaker," filed May 23, 2013.
Ostroff et al.; U.S. Appl. No. 13/910,896 entitled "Leadless Pacemaker with Multiple Electrodes," filed Jun. 5, 2013.
Ostroff, Alan; U.S. Appl. No. 13/915,560 entitled "MRI Compatible Leadless Cardiac Pacemaker," filed Jun. 11, 2013.
Ostroff, Alan; U.S. Appl. No. 13/967,180 entitled "Leadless Cardiac Pacemaker with Secondary Fixation Capability" filed Aug. 14, 2013.

\* cited by examiner

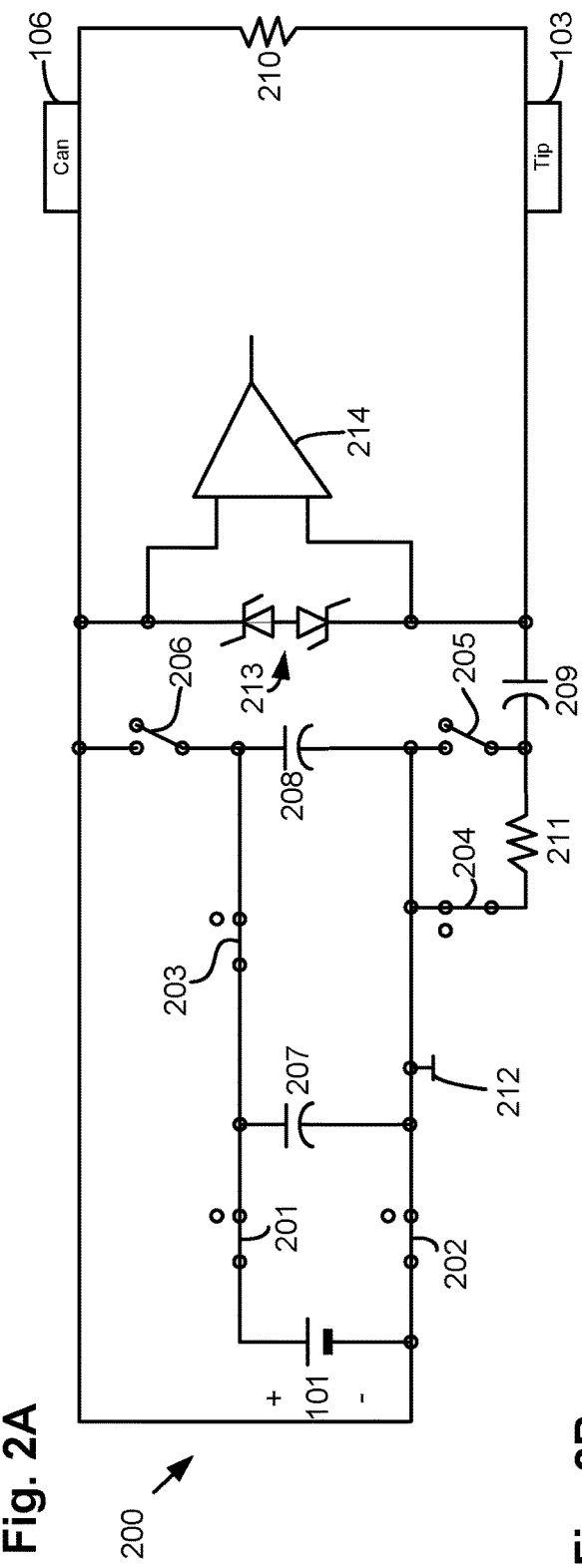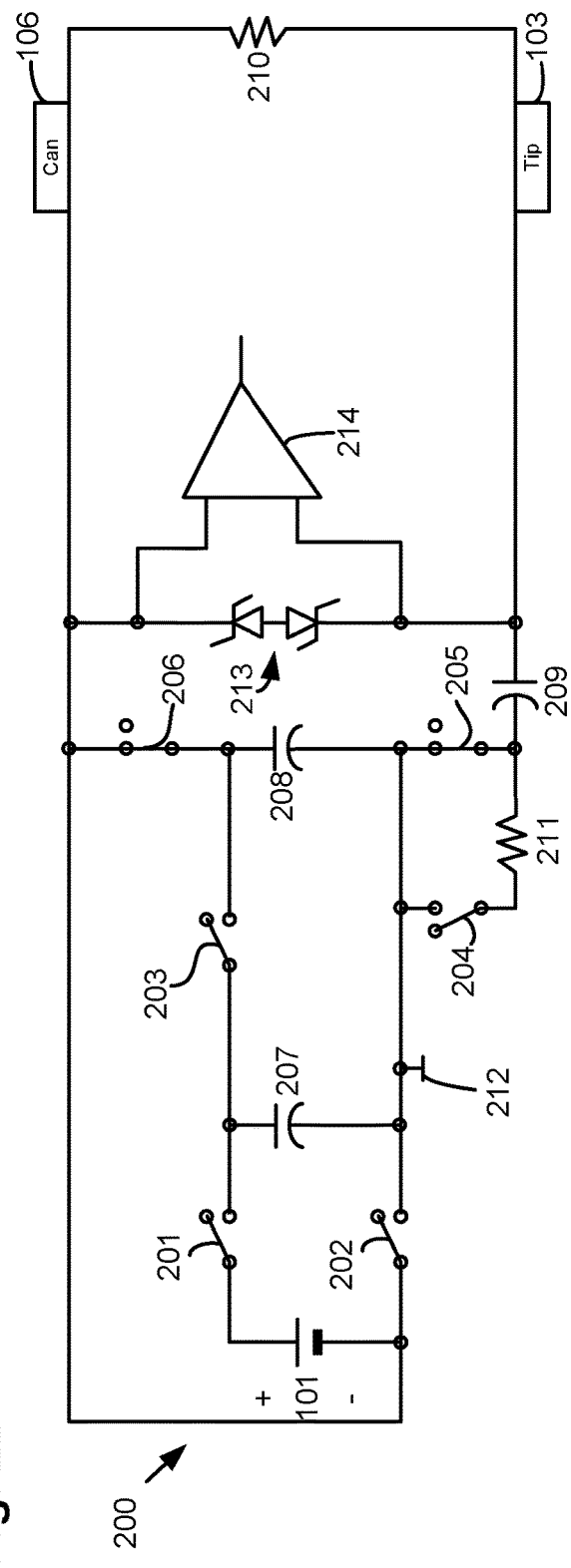

BIOSTIMULATOR CIRCUIT WITH FLYING CELL

CROSS-REFERENCE TO RELATED APPLICATIONS

This application is a divisional of U.S. patent application Ser. No. 13/956,946, filed Aug. 1, 2013, published as U.S. Pub. No. 2014/0039570 and issued as U.S. Pat. No. 9,802,054 on Oct. 31, 2017, which claims the benefit of U.S. Provisional Patent Application No. 61/678,505, filed on Aug. 1, 2012, titled "Biostimulator Circuit with Flying Cell", the contents of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to implantable pacemakers or biostimulators. More specifically, this disclosure relates to improved implantable leadless pacemakers having a reduced weight and volume.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Pacemakers require at least two electrodes to deliver electrical therapy to the heart and to sense the intracardiac electrogram. Traditionally, pacemaker systems are comprised of an implantable pulse generator and lead system. The pulse generators are implanted under the skin and connected to a lead system that is implanted inside the heart with at least one electrode touching the endocardium. The lead system can also be implanted on the epicardial surface of the heart.

Pacemaker lead systems are typically built using a unipolar design, with an electrode at the tip of the lead wire, or bipolar design, with an additional electrode ring often 10 mm proximal to the tip electrode. Additionally, the implanted pulse generator can is often used as a pace/sense electrode. In a conventional pacemaker system, pacing occurs either between the electrode tip and ring, or between the tip and can. Likewise, sensing occurs either between the electrode tip and ring or between the tip and the can.

SUMMARY OF THE DISCLOSURE

A leadless cardiac pacemaker, comprising an electronics housing, pacing electronics disposed in the electronics housing, a tip electrode electrically coupled to the pacing electronics, a cell housing, and an energy source disposed in the cell housing, the energy source having a positive terminal electrically coupled to the pacing electronics, and a negative terminal electrically coupled to the cell housing, the pacing electronics being configured to drive the tip electrode negative with respect to the cell housing during a stimulation pulse.

In some embodiments, electrically coupling the negative terminal to the cell housing configures the cell housing to act as a can electrode.

In one embodiment, the pacing and sensing electronics comprise at least one p-type substrate.

In additional embodiments, the energy source comprises at least one lithium carbon mono-fluoride cell.

In some embodiments, the pacemaker does not include an additional housing or ring electrode disposed around the cell housing.

In one embodiment, the pacemaker is configured to provide stimulation pulses from the cell housing to the tip electrode through cardiac tissue.

In some embodiments, the pacing electronics permit the cell housing which is coupled to the negative terminal of the energy source to serve as a positive can electrode during the stimulation pulse.

In another embodiment, the pacing electronics include at least one switch that prevent the passage of current in the presence of defibrillation or electrosurgery voltages on a high terminal of the at least one switch.

A method of driving a leadless pacemaker is also provided, comprising the steps of coupling a negative terminal of a cell to a cell housing of the leadless pacemaker, coupling a positive terminal of the cell to p-type substrate pacing electronics of the leadless pacemaker, driving, with the pacing electronics, a tip electrode of the leadless pacemaker negative with respect to the cell housing during a stimulation pulse.

In one embodiment, the method further comprises the step of stimulating cardiac tissue with the stimulation pulse.

In some embodiments, the driving step comprises driving the tip electrode as a negative electrode and driving the cell housing as a positive electrode during the stimulation pulse.

A leadless cardiac pacemaker is also provided, comprising a tip electrode, pacing electronics disposed on a p-type substrate in an electronics housing, the pacing electronics being electrically connected to the tip electrode, and an energy source disposed in a cell housing, the energy source comprising a negative terminal electrically connected to the cell housing and a positive terminal electrically connected to the pacing electronics, the pacing electronics being configured to drive the tip electrode as a negative electrode and the cell housing as a positive electrode during a stimulation pulse.

In some embodiments, the energy source comprises at least one lithium carbon mono-fluoride cell.

In another embodiment, the pacemaker further comprises a fixation feature configured to affix the pacemaker to cardiac tissue.

In one embodiment, there is no separate housing disposed around the cell housing.

In another embodiment, the cell housing is configured to act as a can electrode.

In yet another embodiment, there is no separate ring or can electrode disposed around the cell housing.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2B provide schematic diagrams of pacing electronics according to one embodiment.

DETAILED DESCRIPTION

Figure 1:
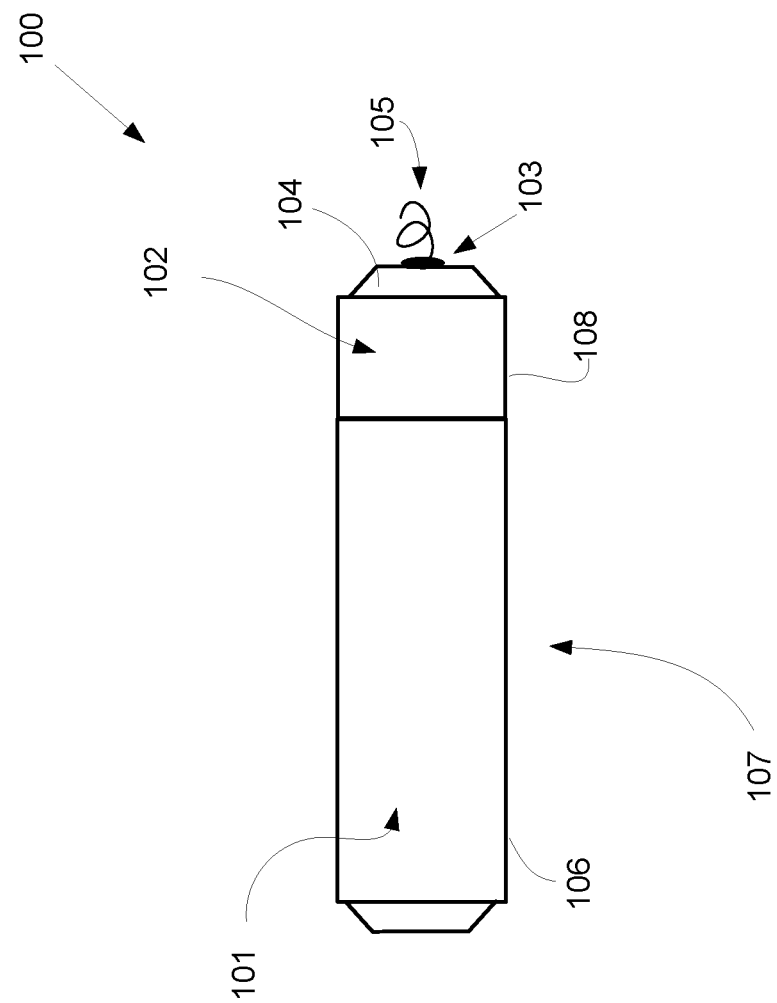
FIG. 1 shows an external view of a biostimulator or leadless pacemaker.

Leadless pacemaker designs described in the present disclosure provide improvements over conventional pacemakers with leads and also over prior leadless pacemaker designs. The leadless pacemaker designs described herein advantageously minimize biostimulator volume while increasing efficiency and cell life. Six design techniques described herein contribute to reducing biostimulator volume.

First, the housing of the device's energy source can be used as part of the housing of the stimulator. This provides more compact construction than that of conventional pacemakers, which generally include a first metal housing containing the energy source, entirely enclosed within a second metal housing containing the energy source housing, along with circuitry.

Second, an energy source with high energy per unit volume and low internal resistance can be used within the leadless pacemaker. Both features decrease the amount of reactants necessary for a specified device lifetime.

Additionally, the device's analog and digital functions can be implemented with a single integrated circuit. This reduces board area, encapsulation volume, and interconnection area, thereby allowing all the internal circuitry of the pacemaker to be contained within a smaller housing and reducing overall biostimulator volume.

Fourth, the pacemaker can have a generally cylindrical form with diameter not to exceed 7 mm, and preferably having a diameter that does not exceed 6 mm. In some embodiments, pacemakers utilizing the design of this disclosure can have dimensions of approximately 6 mm in diameter and approximately 3.5 cm in length, for a total volume of approximately 1 cc and a mass of approximately 2 gm. This enables percutaneous delivery of the biostimulator through the vasculature. To provide high energy per unit volume and low internal resistance with this form, chemical cell manufacturers propose lithium carbon monofluoride ("CFx") cells with "bobbin" construction, symmetric around the cell's long axis, with the lithium anode arranged along the cell housing's inside wall. Thus, in some embodiments the cell housing forms the cell's negative terminal ("negative can").

Another improvement includes providing efficient stimulation via a first small-surface-area electrode ("tip"), and a second large-surface-area electrode ("ring" or "can"). The small tip provides a high electric field gradient to induce stimulation. The large ring or can provides a low spreading resistance to minimize electrical losses. To prevent corrosion, arrhythmia induction, and elevated pacing thresholds, stimulators generally provide a pulse with the tip negative with respect to the can ("positive can").

Finally, another improved disclosed herein includes implementing mixed analog and digital functions on a single integrated circuit with minimal substrate area. In some embodiments, the integrated circuits used in the leadless pacemakers described herein can include only p-type processes where no point on the chip can have a voltage below the substrate voltage ("negative ground").

FIG. 1 shows an external view of a leadless pacemaker or biostimulator 100. The pacemaker 100 can comprise energy source or cell 101, pacing electronics 102, tip electrode 103, insulator 104, and fixation feature 105. Electronics 102 can include a single p-type substrate ASIC. The pacemaker 100 can comprise an outer housing 107, which in this embodiment is a combination of cell housing 106 (surrounding cell 101) and circuit housing 108 (surrounding electronics 102). The cell housing 106 can act as an electrode (e.g. a ring electrode). In some embodiments, the housings can comprise a conductive material such as titanium, 316L stainless steel, or other similar materials. The fixation feature 105 can comprise a fixation helix or other screw-like feature configured to affix the pacemaker to cardiac tissue.

In the embodiment of FIG. 1, the negative terminal of the energy source 101 can be connected to the cell housing 106, and the positive terminal of the cell can be connected to electronics 102 within circuit housing 108. By connecting the negative terminal of the energy source to the cell housing, the cell housing can then be used as a ring or can electrode for the pacemaker. Since the cell housing 106 is connected to the negative terminal of the energy source 101 so as to act as a can electrode, the combination can be referred to collectively within this disclosure as the "negative can", "can electrode", or "ring electrode". Utilizing the cell housing as the negative can allows the pacemaker 100 to be designed without requiring an additional pacemaker housing and/or ring electrode around the energy source and cell housing, which can significantly reduce the size and cost of the pacemaker.

Insulator 104 can be configured to electrically isolate tip electrode 103 from the rest of the device, including from the electronics and the negative can. The insulator 104 can include a ceramic to metal feedthrough or a glass to metal feedthrough to connect the tip electrode to electronics 102, as known in the art. The tip electrode 103 can be, for example, a raised or "button" shaped electrode disposed on a distal tip of the housing. The tip electrode can be other shapes, including square, rectangular, circular, flat, pointed, or otherwise shaped as known in the art. In additional embodiments, the electrode can be integrated into the fixation feature 105.

When the pacemaker of FIG. 1 is activated, stimulation current can flow from the cell housing 106, at positive polarity during the stimulation pulse, to tip electrode 103, at negative polarity during the stimulation pulse. Consequently the cell housing 106 also serves as the positive ring electrode during stimulation. Insulator 104 separates the cell housing (acting as a ring or can electrode) from the tip electrode 103, both physically and electrically during use. In order for the pacemaker 100 of FIG. 1 to function properly when implanted in a heart of a patient, the tip electrode 103 must be driven negative with respect to the ring or can electrode (e.g., cell housing 106) even though the cell's negative terminal is connected directly to the ring or can electrode.

Traditionally, n-type substrate technology was available to pacemaker and pacemaker designers, who could connect the positive terminal of the cell to the n-type substrate and to the ring electrode, allowing the negative terminal of the cell to create a negative voltage that would be commuted to the tip electrode. However, it is presently difficult to find n-type substrates for use in these applications, so the present invention advantageously allows the tip electrode to be driven negative with respect to the ring electrode while using a p-type substrate.

FIGS. 2A-2B are simplified schematic diagrams of pacing and sensing circuitry 200, according to one embodiment. The pacing and sensing circuitry 200 can be all or a portion of the circuitry found in electronics 102 of FIG. 1. Reference to can electrode 106 and tip electrode 103 can also be referring to the electrodes of FIG. 1.

In the illustrated embodiment, the pacing and sensing circuitry 200 can be a single p-type substrate ASIC. This circuitry allows the tip electrode of a pacemaker to be driven negative with respect to the can electrode when constrained to using a p-type substrate and a lithium CFx cell. FIG. 2A shows switches 201-206 in a first state, occurring between stimulation pulses, with switches 201-204 closed and switches 205-206 opened. FIG. 2B shows switches 201-206 in a second state, occurring while delivering a stimulation pulse, with switches 201-204 opened and switches 205-206 closed.

In the first state, energy source 101 (which can be the energy source 101 from FIG. 1) charges cell tank capacitor 207 and pacing tank capacitor 208, through switches 201-203.

In the second state, the energy source 101 is switched out of the circuit and pacing tank capacitor 208 discharges through switches 205-206 through body load 210 and output coupling capacitor 209, forcing the tip electrode 103 to go negative with respect to the can electrode 106. When the biostimulator 100 described above operates in the second state, stimulation current flows from the can electrode (positive electrode, also shown as cell housing 106 in FIG. 1) to the electrode tip (negative electrode, shown as tip electrode 103 in FIG. 1).

Returning to the first state, output coupling capacitor 209 discharges through switches 202 and 204, and body load 201. This ensures charge balance through the electrodes. Resistor 211 represents the on-resistance of switch 204, selected to limit this charge-balancing current. The resistance of resistor 211 can be chosen based on several factors, including the stimulation frequency, load impedance, and effective output capacitance.

Integrated circuit ground 212 consequently is the most negative voltage in the system. During the stimulation pulse (e.g., when the circuit is in the second state), the negative terminal of energy source 101 "flies up" from ground to the stimulating voltage on the positive terminal of pacing tank capacitor, and the positive terminal of energy source 101 "flies up" even higher but is disconnected. Cell tank capacitor 207 maintains a supply voltage for other circuits (not shown). After completion of the stimulation pulse, the cell "flies down" so that its negative terminal is reconnected to ground and its positive terminal is reconnected to the positive terminal of cell tank capacitor 207. This "flying cell" configuration permits the cell negative terminal—the negative cell housing or can electrode—to serve as the positive ring or can for stimulation.

Protection device or devices 214 limit voltage between the can electrode 106 (which is the negative terminal of energy source 101) and the tip electrode 103, to protect the circuit 200 during defibrillation or electrosurgery. The circuit 200 may include a sensing amplifier as the protection device 214 to detect intrinsic or evoked activity in the stimulated organ. The amplifier can detect potentials between tip 103 and can 106 (housing of energy source 101), and all circuitry in the amplifier can operate above ground potential 212.

A capacitive or inductive voltage converter (not shown) may optionally replace switch 203 to provide efficient charging of pacing capacitor 208 at voltages different from that of energy source 101, as is known in the art.

Figure 3:
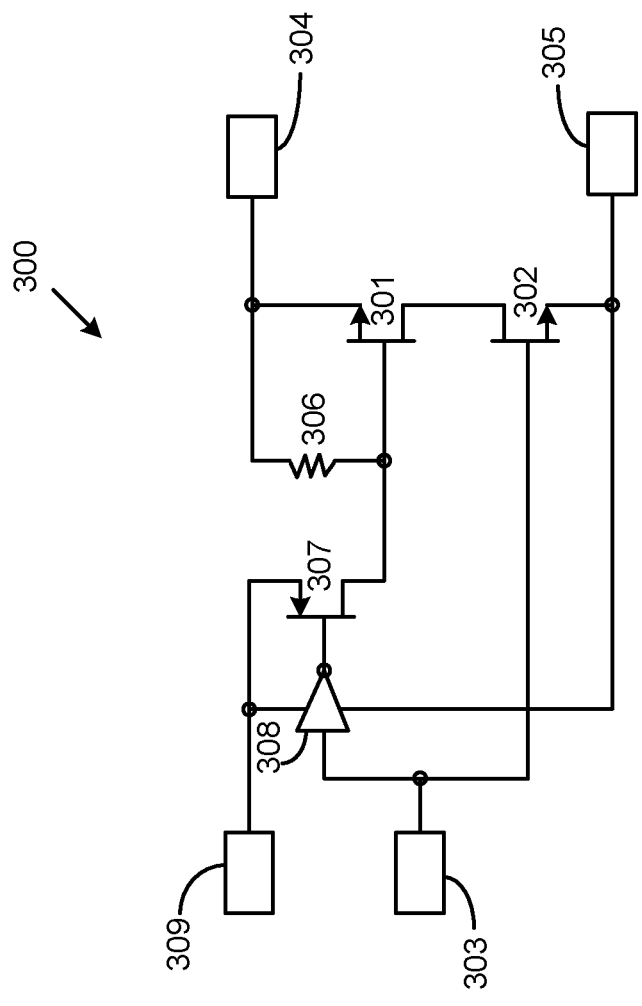
FIGS. 3 and 4 provide detailed diagrams of the implementation of switches in the pacing electronics of FIGS. 2A-2B.

FIG. 3 shows a simplified schematic diagram 300 corresponding to each of switches 204 and 205 from FIGS. 2A-2B, which require a novel implementation because of potential presence of defibrillation or electrosurgery voltages on the tip electrode (such as tip electrode 103 described above). Each switch has a high terminal 304, low terminal 305, control terminal 303, and driver voltage 309. The switch is designed to pass no current in the presence of defibrillation or electrosurgery voltages on the high terminal 304 as limited by protection devices in the circuit (such as protection device 214 above).

When control terminal 303 is low, resistor 306 holds switch 301 off and control terminal 303 holds switch 302 off, even with full protected voltage on 304. Because switches 301 and 302 are connected in opposite configurations, their body diodes do not conduct. When control terminal 303 is driven to the driver voltage 309 (for example, the voltage at the positive terminal of cell tank capacitor 207 from FIGS. 2A-2B), switch 302 turns on, and switches 308 and 307 turn switch 301 on.

Figure 4:
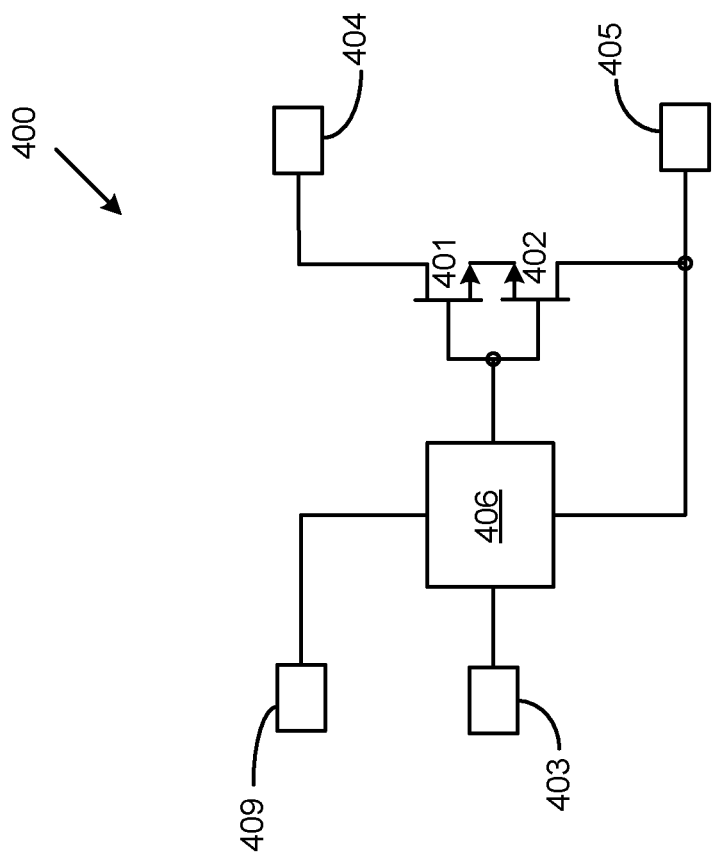

FIG. 4 shows a simplified schematic diagram 400 of switch 206 from FIGS. 2A-2B, which requires novel implementation because of potential presence of defibrillation or electrosurgery voltages on the can electrode (such as housing 106 described above). The switch has a high terminal 404, low terminal 405, control terminal 403, and driver voltage 409. The switch is designed to pass no current in the presence of defibrillation or electrosurgery voltages on the high terminal 404 as limited by protection device 214. When control terminal 403 is low (at the voltage of 405), level shifter 406 output is at the voltage of 405, which holds switches 401 and 402 off, even with full protected voltage on 404. Because switches 401 and 402 are connected in opposite configurations, their body diodes do not conduct. When control terminal 403 is driven to the driver voltage 409 (in this case the voltage at the positive terminal of energy source 101, which during stimulation is higher than the can electrode voltage), then switches 401 and 402 turn on.

Switches 201 and 203 of FIGS. 2A-2B may each be implemented with a P-channel MOSFET, and switch 202 may be implemented with an N-channel MOSFET, all in a conventional manner.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of operating a leadless pacemaker having pacing electronics, a tip electrode electrically coupled to the pacing electronics, a can electrode comprising at least a portion of a cell housing, and an energy source disposed in the cell housing and having a negative terminal electrically connected to the cell housing, the method comprising:
during a first state, closing a first set of switches of the pacing electronics to electrically connect the pacing electronics to the energy source and to electrically connect a first capacitor and a second capacitor to the energy source; and
during a second state:
opening the first set of switches to electrically disconnect the pacing electronics from the energy source such that the pacing electronics are powered by the first capacitor, and
closing a second set of switches such that the second capacitor is discharged into the cell housing, thereby driving the tip electrode negative with respect to the can electrode.

2. The method of claim 1, further comprising, during the second state, discharging a third capacitor through the first set of switches of the pacing electronics to cause a charge balance between the tip electrode and the can electrode of the leadless pacemaker.

3. The method of claim 1, further comprising using a protection device to limit a voltage difference between the can electrode and the tip electrode during the second state.

4. The method of claim 3, wherein the using the protection device comprises using a sensing amplifier to detect intrinsic or evoked activity.

5. The method of claim 3, wherein the using the protection device comprises using a sensing amplifier to detect a potential between the tip and can electrodes, and wherein the method further comprises operating all circuitry in the sensing amplifier above an integrated circuit ground potential.

6. The method of claim 1, wherein at least one switch of the second set of switches comprises a high terminal, a low terminal, a control terminal, and a driver voltage, and wherein during the second state, the at least one switch passes no current in a presence of defibrillation electrosurgery voltages on the high terminal.

7. The method of claim 6, wherein the at least one switch of the second set of switches comprises a first switch and a second switch connected in opposite configurations such that respective body diodes of the first and second switches do not conduct current, and wherein the method further comprises, when the control terminal is low, holding the first switch off using a resistor and holding the second switch off using the control terminal.

8. The method of claim 7, wherein the at least one switch of the second set of switches further comprises a third switch and a fourth switch, the method further comprising turning the second switch on by driving the control terminal to the driver voltage, and using the third and the fourth switches to turn the first switch on.

9. The method of claim 6, wherein the at least one switch of the second set of switches comprises a level shifter and a first switch and a second switch connected in opposite configurations such that respective body diodes do not conduct current, and wherein the method further comprises, when the control terminal is at a voltage of the low terminal, holding the first and second switches off using the level shifter.

10. The method of claim 9, further comprising turning the first switch and the second switch on by driving the control terminal to a same voltage as the driver voltage.

11. A method of operating a leadless cardiac pacemaker having pacing electronics, a tip electrode electrically coupled to the pacing electronics, a cell housing, an energy source disposed in the cell housing having a negative terminal electrically connected to the cell housing, the method comprising:
during a first state:
powering the pacing electronics using the energy source; and
charging at least a first capacitor and a second capacitor using the energy source; and
during a second state used to deliver a stimulation pulse:
disconnecting the first capacitor from the energy source and the tip electrode;
electrically connecting the first capacitor to the pacing electronics and powering the pacing electronics using the first capacitor; and
discharging the second capacitor into the cell housing, resulting in the cell housing serving as a positive terminal with respect to a negative terminal formed at the tip electrode during delivery of the stimulation pulse.

12. The method of claim 11, further comprising stimulating cardiac tissue with the stimulation pulse.

13. The method of claim 12, further comprising using at least one switch to prevent passage of electricity between the pacing electronics and the cell housing during the second state.

14. The method of claim 12, wherein the energy source comprises a lithium carbon mono-fluoride cell.

* * * * *